United States Patent
Denny

(10) Patent No.: US 9,993,226 B2
(45) Date of Patent: Jun. 12, 2018

(54) DEVICE AND METHOD FOR DETECTING SKIN TO MUSCLE DEPTH BY SIMULTANEOUS DETECTION OF ULTRASONIC DEPTH SENSOR AND FORCE SENSOR

(71) Applicant: MYLAN INC., Morgantown, WV (US)

(72) Inventor: John W. Denny, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 150 days.

(21) Appl. No.: 14/564,793

(22) Filed: Dec. 9, 2014

(65) Prior Publication Data
US 2016/0157816 A1 Jun. 9, 2016

(51) Int. Cl.
*A61B 8/08* (2006.01)
*A61M 5/32* (2006.01)
(Continued)

(52) U.S. Cl.
CPC .......... *A61B 8/0858* (2013.01); *A61B 5/0022* (2013.01); *A61B 5/0053* (2013.01); *A61B 5/1075* (2013.01); *A61B 5/4519* (2013.01); *A61B 5/6843* (2013.01); *A61B 8/085* (2013.01); *A61B 8/4427* (2013.01); *A61B 8/5223* (2013.01); *A61B 17/3403* (2013.01); *A61B 19/46* (2013.01); *A61M 5/20* (2013.01);
(Continued)

(58) Field of Classification Search
CPC .................................................. A61B 8/0858
See application file for complete search history.

(56) References Cited

U.S. PATENT DOCUMENTS 3,933,148 A 1/1976 Wyler et al.
9,636,084 B2 * 5/2017 He ....................... A61B 8/0858
(Continued)

FOREIGN PATENT DOCUMENTS

AR 102896 A1 3/2017
EP 3229685 A1 10/2017
(Continued)

OTHER PUBLICATIONS

Lyness Thesis 2013_Understanding the key parameters affecting needle free skin penetration by a parental drug delivery system.*

(Continued)

*Primary Examiner* — Serkan Akar

(57) ABSTRACT

The hand-held device detects the distance between a muscle and an outer skin layer in a body by impacting the outer surface of the skin and detecting the distance to the muscle from that point of engagement. The device includes a first end including a force sensor configured to detect the force of an impact of the first end to an associated body part. The device further includes a distance sensor provided at the first end configured to detect the distance between a skin outer layer and a muscle; and a main body configured to receive a hand. The detection device includes a controller and processor to detect the impact force and distance between the skin outer layer and muscle at engagement. The device may be used in a method of determining muscle depth and/or location in connection with the prescription and/or administration of anaphylaxis medications by auto injector.

16 Claims, 6 Drawing Sheets

(51) Int. Cl.
*A61B 17/34* (2006.01)
*A61B 19/00* (2006.01)
*A61B 5/00* (2006.01)
*A61B 5/107* (2006.01)
*A61M 5/20* (2006.01)
*A61M 5/46* (2006.01)
*A61B 8/00* (2006.01)
*A61B 5/11* (2006.01)

(52) U.S. Cl.
CPC ............ *A61M 5/32* (2013.01); *A61M 5/3286* (2013.01); *A61M 5/46* (2013.01); *A61B 5/1107* (2013.01); *A61B 8/4488* (2013.01); *A61B 8/565* (2013.01); *A61B 2017/3413* (2013.01); *A61B 2019/464* (2013.01); *A61B 2505/01* (2013.01); *A61B 2562/0247* (2013.01); *A61B 2562/0252* (2013.01); *A61M 2205/332* (2013.01); *A61M 2205/3306* (2013.01)

(56) References Cited

U.S. PATENT DOCUMENTS

| | | | |
|---|---|---|---|
| 9,642,593 B2 * | 5/2017 | Sarnow | A61B 8/0858 |
| 2006/0184024 A1 * | 8/2006 | Da Silva | A61B 8/4281 600/438 |
| 2011/0112397 A1 * | 5/2011 | Shen | A61B 34/20 600/424 |
| 2013/0123629 A1 * | 5/2013 | Rosenberg | A61B 8/0858 600/442 |
| 2014/0020476 A1 | 1/2014 | Inoue et al. | |

FOREIGN PATENT DOCUMENTS

| | | |
|---|---|---|
| JP | 2000233021 A | 8/2000 |
| SU | 891036 A1 | 12/1981 |
| TW | 201628558 A | 8/2016 |
| WO | 02060325 A1 | 8/2002 |
| WO | 2005002428 A1 | 1/2005 |
| WO | 2007066301 A1 | 6/2007 |
| WO | 2009141755 A1 | 11/2008 |
| WO | 2016094125 A1 | 6/2016 |

OTHER PUBLICATIONS

Harold Alexander, "Determining Skin Thickness with Pulsed Ultra Sound", 1979.
Yong-Ping, "An ultrasound indentation system for biomechanical properties assessment of soft tissues in-vivo", Sep. 1996.
International Search Report in related PCT Application PCT/US2015/063177 dated Mar. 15, 2016, 3 pages.
International Preliminary Report on Patentability from Related PCT Application PCT/US2015/063177, dated Jun. 13, 2017, 8 pages.

* cited by examiner

DEVICE AND METHOD FOR DETECTING SKIN TO MUSCLE DEPTH BY SIMULTANEOUS DETECTION OF ULTRASONIC DEPTH SENSOR AND FORCE SENSOR

TECHNICAL FIELD

The invention relates to a device for measuring intramuscular depth in the human body. More particularly, the invention relates to a hand-held device, configured to measure muscle location and distance, when the device is applied to the body at a select location.

BACKGROUND

During an intramuscular injection, medication is generally delivered directly into a muscle, such as a thigh or buttocks. Examples of medications administered intramuscularly, include codeine, metoclopramide, and epinephrine. One of the advantages of injecting medication intramuscularly, is that intramuscular injections are generally absorbed into the muscle fairly quickly, in comparison to other types of injections, such as subcutaneous injections, which have a more gradual absorption rate. Intramuscular injections into body locations, such as the buttocks, and/or thigh, are generally known to reach the bloodstream fairly quickly, due to the large amount of muscular tissue and corresponding blood supply.

The ability to perform an intramuscular injection with accuracy and speed is vital. While most intramuscular injections are administered to patients by trained medical professionals, such as doctors, nurses or physician assistants, self-administered intramuscular injections are becoming more common for patients who require these injections either routinely or immediately. In such cases, the aforementioned medical professionals are typically unavailable. Immediate administration is particularly important when treating illnesses such as Anaphylaxis, in which a serious allergic reaction is rapid in onset, and may cause death if not treated with speed and accuracy.

In general, anaphylaxis may be treated by administration of epinephrine, as well as other medications. Patients are typically prescribed an auto-injector of epinephrine, such as an Epipen® to treat sudden anaphylaxis. Some of the challenges when self-administering epinephrine is that it is not only critical that the medication is administered in a timely manner, it is also important that the dosage is effectively administered into the muscle for rapid distribution. By design, auto-injectors are generally easy to use and intended for self-administration by patients, or untrained individuals. Most auto-injectors are spring-loaded syringes configured to hold a pre-determined dosage of medication. A user suffering from anaphylaxis has a limited amount of time to make a proper injection. Accordingly, failure to inject medication during illness, within a certain time frame, can be fatal.

Conventional injection devices, such as the Epipen®, are usually prescribed to a patient based on the patient's size. Some auto-injectors provide that the needle size can be varied. Providing the proper needle size or auto-injector size is critical, as the intramuscular injection depth varies based on several factors, including the size of patient, and the density of tissue layers between the outer layer and muscle. For example, the muscle depth of a large 300 pound person with thick layers of adipose is greater than that of a thin 50 pound small child.

While, the injection depth of the auto-injector can be adjustable or fixed, it is vitally important that the injection depth is accurate. For example, with regard to Epipen® having a needle length of 14.3 mm, the anterolateral thigh (Vastuslateralis) is the appropriate location for injection. Other known intramuscular injection guidelines for vaccination provide that infants under the age of 18 months should have a needle length generally between ⅝"-1" (16 mm-25 mm) and injections should be made into the Vastuslateralis muscle. The guidelines further provide that children older than 18 months and under the age of 18 should have needle lengths between ⅞"-1¼"(22 mm-32 mm) and injections should be made into the Deltoid muscle, Ventrogluteal site, Dorsogluteal site or Vastuslateralis muscle. Guidelines further provide that adults should have a needle length between 1"-1½" (25 mm-38 mm) and injections should be made into the Deltoid muscle, Ventroglutealsite, Dorsogluteal site (however not in obese adults) or Vastuslateralis. While these guidelines are instructive, determining the most effective location and needle length may vary based on the actual size of the human being.

Auto-injectors may be activated by pressing a button located on the auto-injector or other firing mechanism, such that the syringe needle is automatically exerted. Most auto-injectors are spring-loaded syringes configured to hold a pre-determined dosage of medication. The medication is then delivered by the auto-injector needle through the outer skin into the muscle with an impactful force. Once the injection is completed, some auto-injectors provide a visual indication to confirm that the full dose has been delivered. While the visual indication feature is helpful, most auto-injectors do not indicate whether the device actually released the medication into the muscle, or accidentally into an organ and/or tissue proximate to the muscle. Failure to contact the muscle on injection can diminish the effectiveness of the dosage. Accordingly, it is important for the user to be able to accurately locate the muscle. It is further important to properly size the auto-injector, such that the needle has the correct length to achieve the proper injection depth, and thus provide effective administration. One existing problem, is that health care professionals do not have a device or method to accurately measure the distance from the outer skin layer, to the muscle upon injection of an auto-injector.

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various exemplary embodiments relate to a hand-held device for detecting distance between a muscle and an outer skin layer in a body. Hand-held detection device includes a first end including a force sensor configured to detect the force of an impact of the first end to an associated body part, a distance sensor provided at the first configured to detect the distance between a skin outer layer and a muscle; and, a main body configured to receive a hand.

In an embodiment of the hand-held device, the distance sensor includes an ultrasonic transducer configured to detect the properties of the epidermis (E), dermis (D), adipose tissue (A) and muscle (M) and the force sensor includes a load cell configured to measure the force of impact.

The method for determining tissue thickness between the skin and the muscle includes the steps of measuring the applied force using the device or sensor. The force measuring sensor may include a load cell operatively connected to the probe head such that forces on the probe head are transmitted to the load cell. The force sensor is flexibly joined to the relatively rigid portion and can move longitudinally. Then applying force with the detection device against an external body tissue with a selected force and detecting the distance between an outer skin layer and muscle layer using ultrasound. Thereafter, the method includes providing a processor for quantifying displacement of internal issues and thereafter, the method includes measuring the force applied to the body tissue and calculating the displacement of the external body tissue. Then the method includes calculating material properties from the measured force and the calculated displacement to calculate the depth to muscle.

The method of diagnosing and/or treating a patient condition using an auto-injector may include several options. In an embodiment, the medical practitioner measures the muscle depth at the thigh or buttock using the detection device and prescribes an auto-injector or injection device with an appropriate needle length and/or prescribes the patient with the most appropriate injection location, based on the muscle detection. In another embodiment, emergency personnel, such as an EMT, uses the muscle depth detector to measure the muscle depth at a location to determine the appropriate needle length and/or injection location. In another embodiment, the detection device is provided for use at a home or office, by a patient or caregiver, for the purposes of measuring muscle depth to determine appropriate needle application location.

BRIEF DESCRIPTION OF THE DRAWINGS

In order to better understand various exemplary embodiments, reference is made to the accompanying drawings, wherein.

DETAILED DESCRIPTION

The depth detection device and method of the invention assists patients and medical professionals in accurately measuring muscle depth in the body during a simulated auto-injector engagement, for the purpose of reducing user error during the self-injection process. By accurately measuring the distance from the outer epidermis layer to the inner muscle, and also measuring the force applied at the impact zone by the device, during an injection, medical service providers may more accurately determine needle size and/or length when prescribing an auto-injection device to a patient. Further, by calculating and instantly reporting the force applied by the patient during a simulated self-injection with the device, medical professionals can more effectively advise patients as to the applied force, when self-injecting.

Because locating the muscle in a large human being or relatively thin human being can be difficult, the depth detection device may be used to locate the muscle in body. Additionally, the device may detect the muscle depth, and indicate to the user when a muscle is located within a pre-selected distance. Accordingly, in view of the aforementioned problems, it is desirable to provide a method and device for detecting application, or engagement force, as well as distance to the muscle during intramuscular injections.

Figures 1A, 1B:
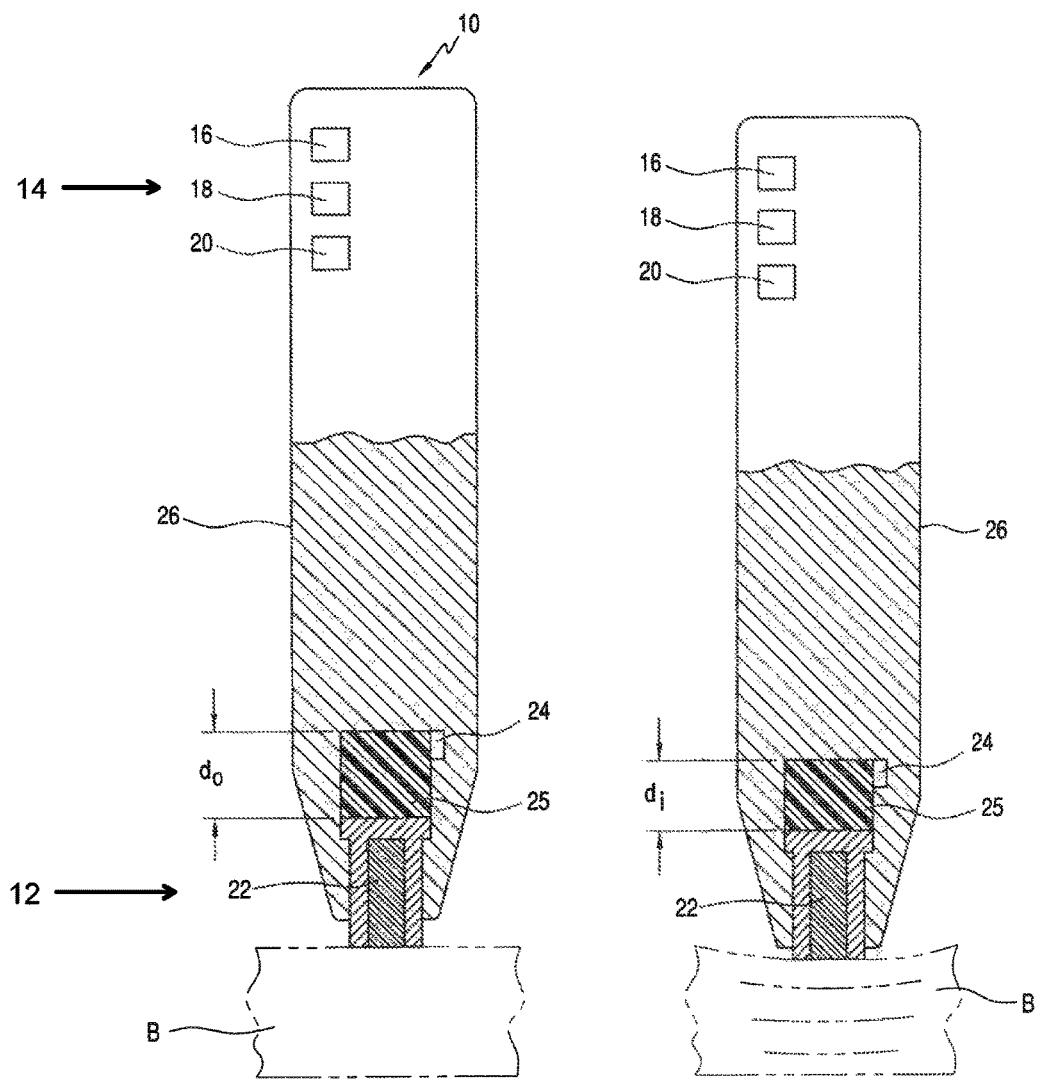
FIG. 1A illustrates a side view of an exemplary muscle depth measuring device for measuring the distance to the muscle from the outer layer of skin using a resilient member.
FIG. 1B illustrates a side view of the device of FIG. 1 illustrating the deflection of the body at the skin layer during detection of muscle depth using a resilient member.

Referring now to the drawings, in which like numerals refer to like components or steps, there are disclosed broad aspects of various exemplary embodiments. FIGS. 1A and 1B illustrate an intramuscular depth detection device, generally indicated at reference numeral 10. The depth detection device 10 is configured for detecting and/or measuring the distance from the outer epidermis of a human and/or mammal, to the muscle (M) at a selected location on the body (B). The depth detection device 10 is configured to simultaneously detect the engagement force applied to body by the depth detection device 10 during simulation, as well as, the distance to the muscle (M) from the depth detection device 10 at the engagement point (P). Using these two measurements, the depth detection device 10 indicates to the user the detected depth to the muscle (M) based on the impact force measured, thereby facilitating needle length selection for a prescribed auto-injection device.

As shown, the depth detection device 10 may be configured in a hand-held configuration, similar to that of an auto-injector, such as an Epipen®, or a similar type apparatus. The depth detection device 10 generally includes a first end, or proximal end 12, configured for engagement with the user's outer skin layer (E), a second end or distal end 14, providing device control features 16-20 for activating one or more detection sensors 22 and 24, and a body 26. Control features 16-20 for the detection device may include an on/off selector 16 for controlling the entire depth detection device 10, a depth activation selector 18 for selectively activating a depth sensor or probe 22, and a force activation selector 20, for selectively activating a force sensor 25.

The configuration of the body 26 of the depth detection device 10 facilitates the user and/or a medical provider to simulate an auto-injector administration. As such, the body 26 has a generally elongated shape, similar to that of an auto-injector. Accordingly, the user may hold the detection device 10 in his/her hand, and apply or engage the body (B) with the detection device 10, such that the first end 12 and sensor 22 engages the surface of the body (B), simulating an intramuscular injection. Upon engagement, the detection device 10 is configured to measure the impact force F at the engagement location, as well as the distance between the point or location of engagement of the device 10 and the muscle (M).

The force sensor 24 is configured to detect the force applied to the body (B) during simulation of detector 10 engagement. As shown in FIGS. 1A and 1B, the force sensor 24 is generally located adjacent to the proximal end of the device 10 to detection the engagement force of the detector 10 with the body (B). The pressure sensor 24 may use a resilient member 25 having a resilient composition, such as for example, a spring, rubber, epoxy, polymer. The force sensor 24 is configured to detect the movement of the resilient member 25 during engagement. By measuring deflection distance $(d_0-d_1)$ of the resilient member 25, and time (t) of engagement, the force applied at engagement may be calculated.

Figures 2A, 2B:
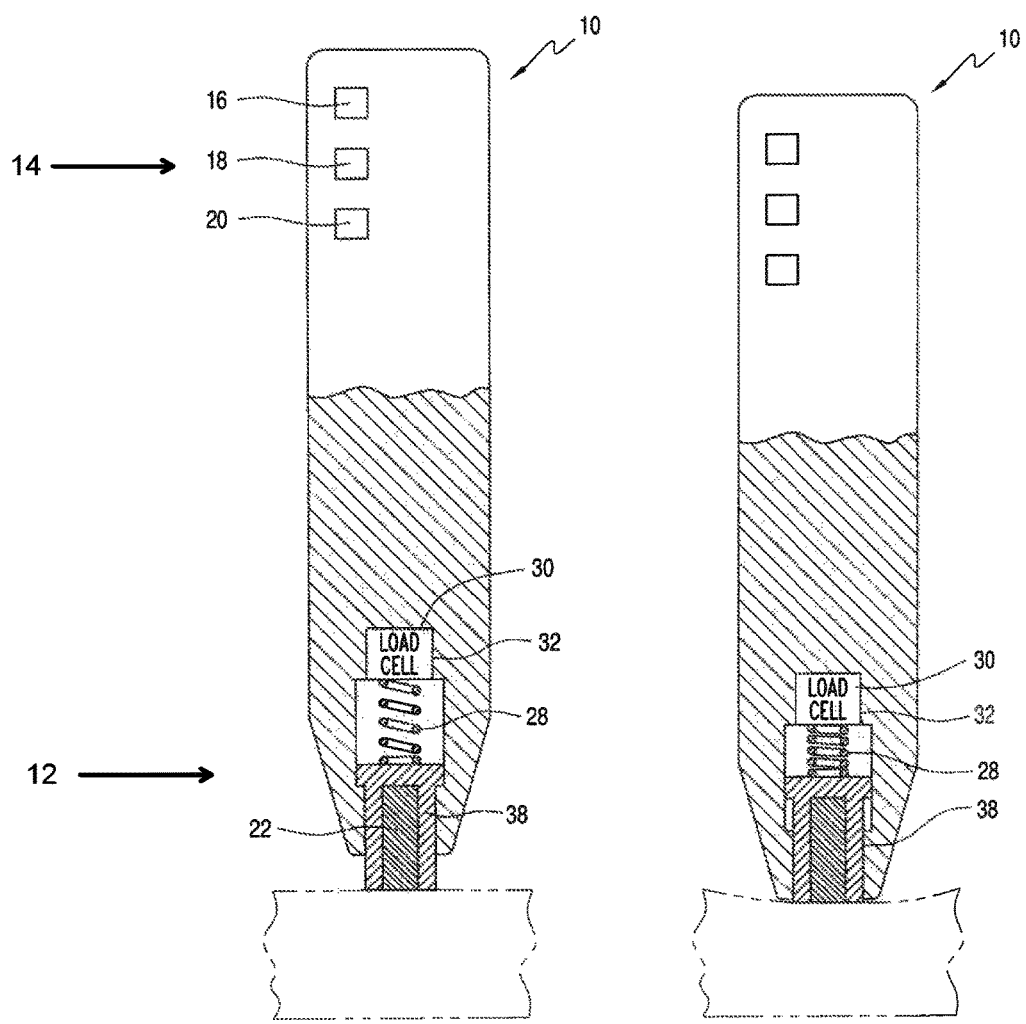
FIG. 2A illustrates a muscle depth detection device using a load cell to detect force.
FIG. 2B illustrates the muscle depth detection device of FIG. 2A illustrating the deflection of the body using a load cell during the detection of muscle depth.

In another embodiment illustrated in FIGS. 2A and 2B, the pressure sensor 24 includes a load cell 30 located proximate to the proximal end 12 of the device 10. The load cell 30 has a relatively rigid housing 32. The load cell 30 may be mounted such that a biased portion 36 of the load cell 30 is biased against a slideable member 38 inside a probe head housing 40 located at the proximal end 12. The slideable member 38 is configured to move freely in at least two directions in the longitudinal dimension L shown.

Accordingly, upon engagement with a surface, such as the outer skin layer, the slideable member 38, is configured to transfer force from the tip of the force sensor 24 to the load cell 30. The load cell 30 data is transmitted to the depth device 10. Biasing of the load cell 30 to the slideable member 38 can be achieved using a biasing member 28. The biasing member 28 may include a spring for spring loading the load cell 30 against the slideable member 38 with a constant force. Accordingly, the load cell 30 is configured to measure compressive load force data during use of device 10 and this information is transmitted for processing.

Figure 3:
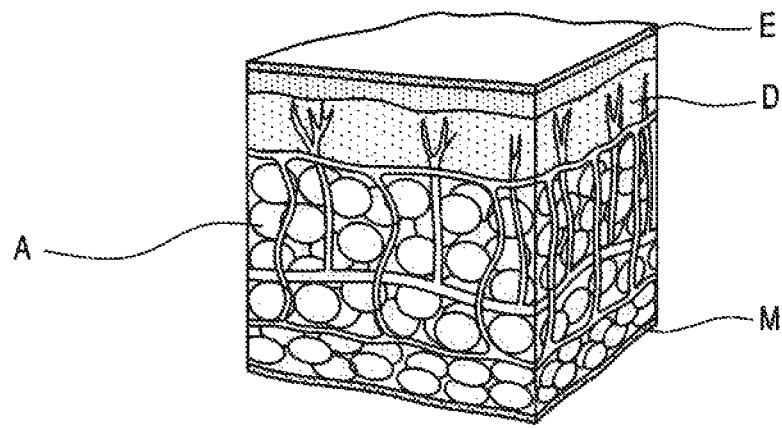
FIG. 3 is a cross-sectional representation of the body layers prior to engagement with the detection device.
Figure 4:
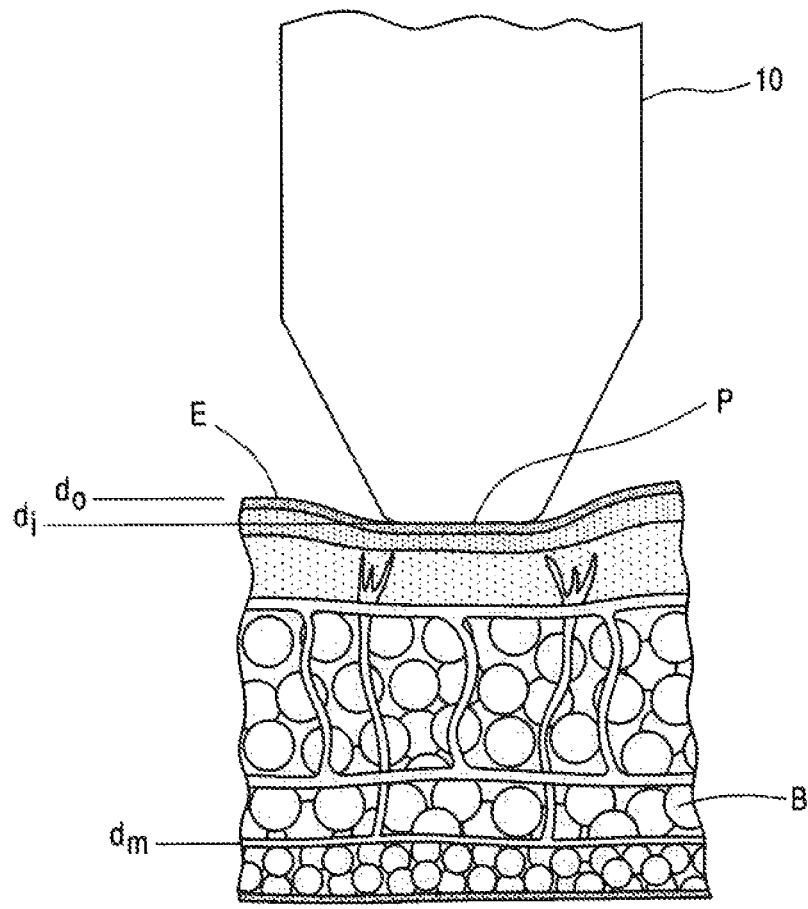
FIG. 4 is a cross-sectional representation of the body layers upon engagement with the depth detection device of FIG. 1A.

In addition to detecting the force upon engagement, the depth detection device 10 is also configured to measure the distance from the layer of skin to the muscle during engagement. To ascertain the muscle depth at an injection location, the depth detection device 10 may measure the distance from the outer skin layer surface (E) to the muscle (M) by calculating the average impact force applied to the outer skin layer (E) by the device 10, and the cumulative distance between the layers located between the outer skin layer surface (E) and muscle (M) during engagement. As shown in FIGS. 3 and 4, the epidermis (E), dermis (D) and adipose tissue (A) are generally are located between the Muscle (M) and outer layer surface. As illustrated in FIG. 4, because the adipose tissue layer (A) is relatively fluid in movement, force applied at the point of application may move the layer (A), thus reducing the distance detected by the depth sensor 24 between $d_1$ and $d_m$ of the muscle (M).

Accurately measuring the distance from impact distance to muscle ($d_1$ to $d_m$) may be achieved using ultrasound.

Figure 5:
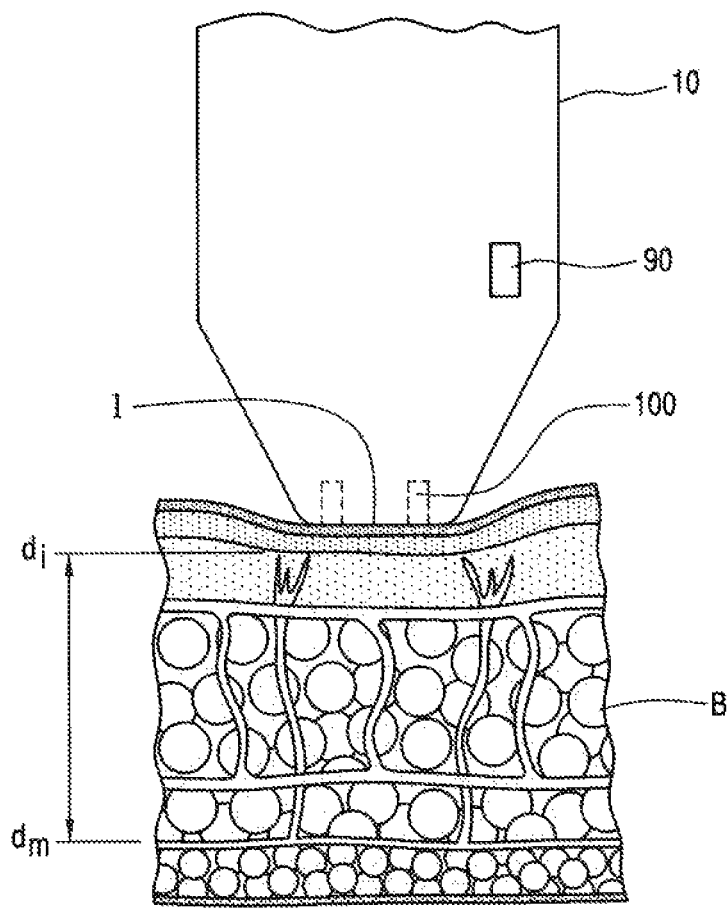
FIG. 5 is a side view of an embodiment of the muscle depth detector illustrating the ultrasonic sensor.

Continuing now to FIG. 5, the depth detection probe 10 may include one or more ultrasound transducers 100 and one or more RF electrodes 102 for measuring the distance from the outer skin layer to muscle upon depth detection 10 engagement ($d_1$ to $d_m$). The muscle depth detection 10 may be configured to include sonography containing multiple acoustic transducers 100, configured to send pulses of sound into the body (B) at the engagement location (I) to ascertain the depth ($d_1$ to $d_m$) to the muscle at that location. Ultrasonography has several advantages. It provides images in real-time (rather than after an acquisition or processing delay) and it is portable, which is desirable when located in the detection device 10. A further advantage of ultrasonography is it is substantially lower in cost, and it does not use harmful ionizing radiation.

The frequencies used for medical imaging are generally in the range of 1 to 18 MHz. Higher frequencies have a correspondingly smaller wavelength, and can be used to make sonograms with smaller details. However, the attenuation of the sound wave is increased at higher frequencies, so in order to have better penetration of deeper tissues, a lower frequency (3-5 MHz) is used.

It is commonly known that the speed of sound varies as it travels through different materials, and is dependent on the acoustical impedance of the material. However, the sonographic sensor 22 may assume that the acoustic velocity is constant at 1540 m/s. The sound reflects and echoes off parts of the tissue layers epidermis (E), dermis (D), adipose tissue (A) and muscle (M). The echo may be recorded and displayed as an image or calculation of distance ($d_1$ to $d_m$) to the operator.

The transducer 100 may be a B-mode type capable of providing images and calculations with a two-dimensional cross-section of the tissue being imaged. The sound wave (SW) transmitted by the ultrasound transducers 100 encounters the multiple layers of epidermis (E), dermis (D), adipose tissue (A), and muscle (M) with different density (acoustical impedance). Accordingly, part of the sound wave is reflected back to the probe 100 and is detected as an echo by the probe 100. The time $t_1$ it takes for the echo to travel back to the probe 100 is measured and used to calculate the depth of the tissue interface causing the echo. The greater the difference between acoustic impedances, the larger the echo is.

If desired, to generate a 2D-image, the ultrasonic beam is swept upon engagement or 1D phased array transducer 100 may be used to sweep the beam electronically. The received data is processed and used to construct an image and calculate distance. The image is then a 2D representation of the slice into the body. In another embodiment, a transducer 100 providing doppler ultrasonography may be used.

Figure 6:
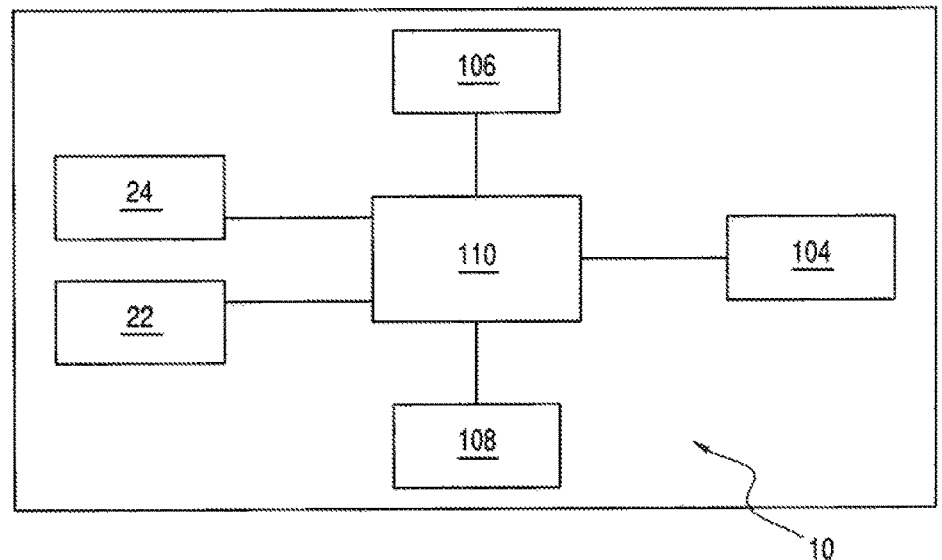
FIG. 6 a systematic illustration of the detection device.

As shown in FIG. 6 a systematic design of the detection device 100 is configured to emit ultrasound beams into the body and/or tissue, and the received reflected beams signals are instantly recorded. The detection device 100 may provide a local memory 104, a controller 110, and processor 108 to calculate, store and process data received from the sensors 22 and 24. As such, distance results may be provided by the display 106. Information and data obtained from the provided in the device 10 or transmitted via Bluetooth to a connected remote controller 110. The controller 110 uses a processor 110 to calculate the tissue profiles and determine the distance from the engagement point (I) to the muscle (M). Further, the controller 110 is configured to provide a profile of the impact force applied.

Figure 8:
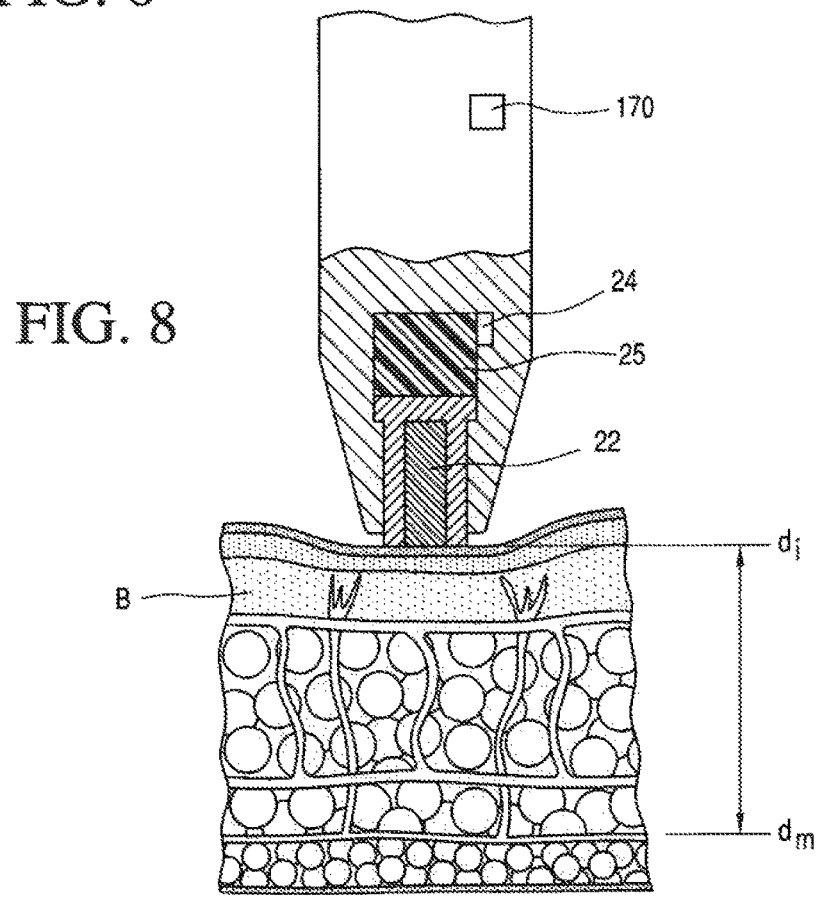
Figure 7:
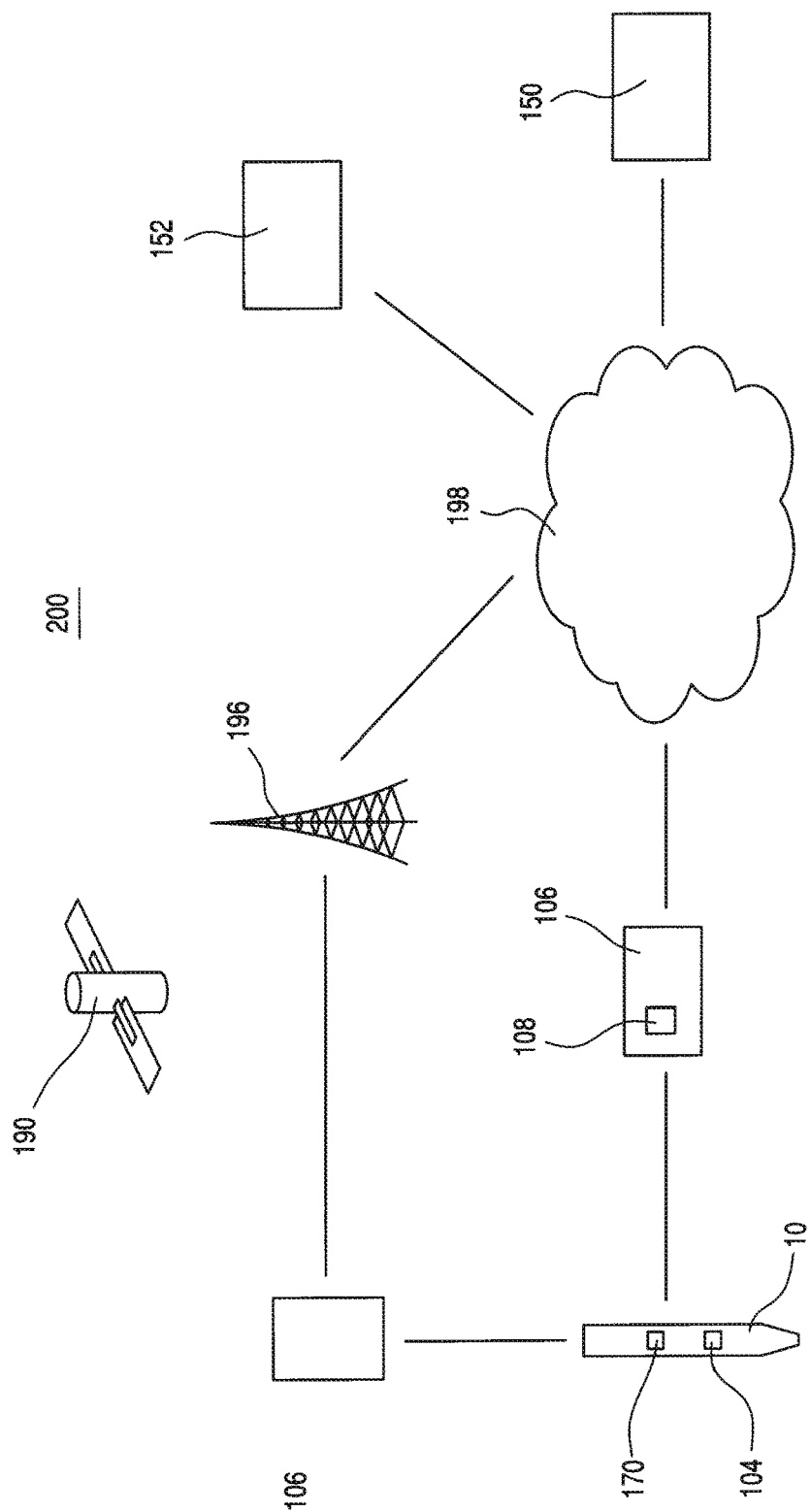
FIG. 7 is an illustration of the detection device in communications with a medication delivery system; and, FIG. 8 is an illustration of the depth detection device in use, showing the depth detection device in an engaging position with the body.

In an embodiment shown in FIG. 8, the muscle detection device 10 uses one or more transducers to detect the location of the muscle. Accordingly, the transducers 100 detect the distance to the muscle and compare the desired distance to a pre-selected distance ($d_s$). In this arrangement, the device 10 may have an indicator 90 that indicates when a muscle is detected within the pre-selected distance ($d_s$). As such, the indicator 90 may use colors, such as green, to indicate when the detection device 10 is detecting a muscle within the pre-selected distance ($d_s$) and a color, such as red, to indicate that the muscle is not within the preselected distance ($d_s$) of the transducer 100.

The detection device 10 may be powered by a wired connection or battery-powered. The detection device 10 may have a wireless transmitter 170, facilitating communication with a medical system 200 and server 150 or may be connected to server 150 through an intermediate wired connection through the system 200. The system 200 may include a cloud computing infrastructure capable of receiving a signal from the smart sensor circuit and/or application 108 and remotely transmitting information to a processor or cloud computer server 150. The transmission hub 106 is in communication with the server or group of servers, which may be connected via a communication network 198 such as the Internet, an intranet, a local area network (LAN), wide area network (WAN), cellular 196, Wi-Fi, for example. The connected transmission hub 106 or application 108 provided on the transmission hub 106 or server 150 includes preselected permissions and protocols permitting communication and remote access to the medical server 150 by the transmission hub 106.

The detection device 10 may further include a storage device or memory 152 in communication with the medical server 150 to store data and information. It is further contemplated that the memory 152 may be provided on the medical server 150 or be externally accessible by the medical server 150. The memory 152 can be any suitable type of computer readable and programmable memory. Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory 152, or in place of memory 152, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. Memory 152 may store information regarding applied force and distance to the muscle ($d_m$) at the point of detection.

It is further contemplated that the depth detection device 10 may be in communication with an application 108 via wireless or Bluetooth technology. The application 108 may be configurable to receive, process and transfer information related to the detection device 10. The application 108 may be stored or provided in a connected medical delivery system's architecture, on a transmission hub 106, such as a smartphone, or remotely on the medical server 150 or connected networks. The connection to the transmission hub 106 facilitates transmission of the depth detection device information remotely.

As such, the application 108 may be configured to monitor a variety of parameters, and/or attributes related to the detection device 10. The application 108 provided on the transmission hub 106, such as a mobile phone, may provide pre-selected information in real-time to the user/patient, as well as any other authorized individuals accessing the mobile device.

As shown in FIG. 8, in operation, the muscle depth detector device 10 may be activated as selected by the user, such that the force detector and ultrasonic detector are simultaneously operable. Notably, it is further contemplated that both depth sensor 22 and force sensor 24 may also be operated separately, if desired. In joint detection, the user grips the detection device 10 about the body (B) and simulates an injection with the device 10, forcefully moving the device 10 towards a desired detection location on the body (B) at a selected speed, or moving the detection device 10 over a selected location of injection. The sensors 22 and 24 located on the proximal end engage the outer layer of the injection portion. The force sensor 22 measures the force applied to the body (B) and with the transducer 100 and transmits this information to the processor 110, including information such as the applied force (F). The depth sensor 22 measures the muscle depth ($d_1$ to $d_m$) to the muscle at that location. This information is transmitted to the medical provider, facilitating the medical provider in selecting a desired needle length, based on the detected depth.

The method of diagnosing and/or treating a patient with an auto-injector may include several options. In an embodiment, a medical practitioner uses the muscle depth detection device 10 to measure muscle depth at a selected point of injection, which may be the buttock or thigh, and prescribes an appropriate auto-injection device with the appropriate needle length, based on the measurements. Based on the depth measurement(s) to the muscle, the practitioner can prescribe an appropriate injection location for an effective auto-injection.

In another embodiment of the method, emergency personnel measures muscle depth at a selected location to determine an appropriate needle length or injection location of the auto-injector device. Based on the muscle depth measurements ($d_m$), the emergency personnel select a correct needle length size or auto-injector size to make an effective injection.

In another embodiment of the method, the patient or caregiver uses the muscle depth detection device 10 to measure the muscle depth to ascertain appropriate injection location. After finding the muscle depth ($d_m$) the detector 10 compares the detected distance to a pre-selected distance ($d_s$) for the auto-injection device. Based on this comparison, the device indicates to the user when the detection device 10 is detecting a muscle ($d_m$) within the pre-selected distance ($d_s$) for the auto-injection device. Accordingly, the user is able to determine appropriate needle location.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications may be affected while remaining within the spirit and scope of the invention. Accordingly, the foregoing disclosure, description, and figures are for illustrative purposes only and do not in any way limit the invention, which is defined only by the claims.

What is claimed is:

1. A hand-held detection device for detecting distances between muscles and outer skin layers in bodies, the hand-held detection device comprising:
    a main body;
    an indicator;
    a first end included in or attached to the main body, the first end including a force sensor configured to detect a force of engagement associated with a displacement of tissues of a body when the first end of the hand-held detection device is placed in a non-penetrative, engaging position with an exterior of a selected body part at an engaging location, the selected body part having an outer skin layer and a muscle;
    an ultrasonic internal body depth sensor provided at the first end and configured to detect, simultaneously with the force sensor detecting the force of engagement, a skin-to-muscle distance between the outer skin layer and the muscle at the engaging location; and
    a processing device that is (i) communicatively coupled to the force sensor and the ultrasonic internal body depth sensor and (ii) included in or attached to the main body, the processing device configured to output data indicating an association among an injection, the force of engagement, and the skin-to-muscle distance;
    wherein the processing device is further configured for:
    comparing the distance detected with the internal body depth sensor to a pre-selected distance corresponding to an auto-injector device; and
    causing, based on the comparison, the indicator to present at least one of
        (i) a first output indicating that the pre-selected distance exceeds the distance detected with the internal body depth sensor or
        (ii) a second output indicating that the distance detected with the internal body depth sensor is less than or equal to the pre-selected distance;
    wherein the hand-held detection device is configured to (i) detect the force of engagement without penetrating the outer skin layer at the engaging location, (ii) detect the skin-to-muscle distance without penetrating the outer skin layer at the engaging location, and (iii) output the data indicating the association without penetrating the outer skin layer at the engaging location.

2. The hand-held detection device of claim 1, wherein the internal body depth sensor includes a probe configured to detect the distance from an epidermis including the outer skin layer to the muscle at the engaging location on the body.

3. The hand-held detection device of claim 2, wherein the probe is an ultrasonic transducer configured to detect the distance between the outer skin layer of skin and the muscle.

4. The hand-held detection device of claim 1, wherein the force sensor includes a load cell configured to measure the force of engagement with the outer skin layer.

5. The hand-held detection device of claim 1, wherein the force sensor includes a resilient member configured to detect the force of engagement applied by the hand-held detection device to the outer skin layer to the muscle.

6. The hand-held detection device of claim 5, wherein the resilient member is a spring.

7. The hand-held detection device of claim 5, further comprising a slideable member positioned at the first end of the hand-held detection device and in operative engagement with the resilient member such that a force applied to the slideable member is transmitted to the resilient member.

8. The hand-held detection device of claim 1, further comprising a display device attached to the main body and configured for displaying the data outputted by the processing device.

9. The hand-held detection device of claim 1, further comprising a transmitter attached to the main body and configured for transmitting, to an external computing device, the data outputted by the processing device.

10. A method for detecting distances between muscles and outer skin layers in bodies, the method comprising:
    providing a hand-held detection device having an indicator, a first end with a force sensor, an ultrasonic internal body depth sensor and a processing device included in or attached to the hand-held detection device that is coupled to the force sensor and the ultrasonic internal body depth sensor;
    placing the first end in a non-penetrative, engaging position with an exterior of a selected body part at an engaging location, the selected body part having an outer skin layer and a muscle;
    detecting, with the force sensor, a force of engagement associated with a displacement of tissues of a body when the first end of the hand-held detection device is placed in the non-penetrative, engaging position;
    detecting, with the ultrasonic internal body depth sensor and simultaneously with the force sensor detecting the force of engagement, a skin-to-muscle distance between the outer skin layer and the muscle at the engaging location; and
    outputting, by the processing device of the hand-held detection device, data indicating an association among an injection, the force of engagement, and the skin-to-muscle distance;
    comparing, by the processing device, the distance detected with the internal body depth sensor to a pre-selected distance corresponding to an auto-injector device; and
    causing, the processing device, based on the comparison, the indicator to present at least one of
        (i) a first output indicating that the pre-selected distance exceeds the distance detected with the internal body depth sensor or
        (ii) a second output indicating that the distance detected with the internal body depth sensor is less than or equal to the pre-selected distance;
    wherein the hand-held detection device with the processor
        (i) detects the force of engagement without penetrating the outer skin layer at the engaging location,
        (ii) detects the skin-to-muscle distance without penetrating the outer skin layer at the engaging location, and
        (iii) outputs the data indicating the association without penetrating the outer skin layer at the engaging location.

11. The method of claim 10, wherein the internal body depth sensor includes a probe that detects the distance from an epidermis including the outer skin layer to the muscle at the engaging location on the body.

12. The method of claim 11, wherein the probe is an ultrasonic transducer that detects the distance between the outer skin layer of skin and the muscle.

13. The method of claim 10, wherein the force sensor includes a load cell that measures the force of engagement with the outer skin layer.

14. The method of claim 10, wherein the force sensor includes a spring that detects the force of engagement applied by the hand-held detection device to the outer skin layer to the muscle using a slideable member positioned at the first end, the slideable member in operative engagement with the spring such that a force applied to the slideable member is transmitted to the spring.

15. The method of claim 10, further comprising displaying, via a display device included in or attached to the hand-held detection device, the data outputted by the processing device.

16. The method of claim 10, further comprising transmitting, via a transmitter included in or attached to the hand-held detection device, the data outputted by the processing device to an external computing device.

* * * * *